(12) United States Patent
Ermanni et al.

(10) Patent No.: US 12,121,459 B2
(45) Date of Patent: Oct. 22, 2024

(54) SELF-EXPANDABLE STENT, METHOD AND DEVICE TO PRODUCE THE SELF-EXPANDABLE STENT

(71) Applicant: ETH Zurich, Zurich (CH)

(72) Inventors: Paolo Ermanni, Zurich (CH); Arthur Schlothauer, Zurich (CH)

(73) Assignee: ETH Zurich, Zürich (CH)

( * ) Notice: Subject to any disclaimer, the term of this patent is extended or adjusted under 35 U.S.C. 154(b) by 409 days.

(21) Appl. No.: 17/279,706

(22) PCT Filed: Aug. 8, 2019

(86) PCT No.: PCT/EP2019/071346
§ 371 (c)(1),
(2) Date: Mar. 25, 2021

(87) PCT Pub. No.: WO2020/052870
PCT Pub. Date: Mar. 19, 2020

(65) Prior Publication Data
US 2022/0110769 A1 Apr. 14, 2022

(30) Foreign Application Priority Data

Sep. 13, 2018 (EP) .................................. 18194304

(51) Int. Cl.
*A61F 2/844* (2013.01)
*A61F 2/24* (2006.01)
*A61F 2/92* (2013.01)

(52) U.S. Cl.
CPC ............ *A61F 2/844* (2013.01); *A61F 2/2418* (2013.01); *A61F 2/2476* (2020.05); *A61F 2/92* (2013.01);
(Continued)

(58) Field of Classification Search
CPC .... A61F 2230/005; A61F 2/24; A61F 2/2412; A61F 2/2415; A61F 2/2418; A61F 2/2469; A61F 2/2475
See application file for complete search history.

(56) References Cited

U.S. PATENT DOCUMENTS 6,165,210 A 12/2000 Lau et al.
2005/0090888 A1 4/2005 Hines et al.
(Continued)

FOREIGN PATENT DOCUMENTS

WO 9526695 A2 10/1995
WO 2005084595 A1 9/2005

OTHER PUBLICATIONS

Holmes et al., 2012 ACCF/AATS/SCAI/STS Expert Consensus Document on Transcatheter Aortic Valve Replacement, J Am Coll Cardiol., Mar. 27, 2012;pp. 1200-1254, vol. 59, No. 13, doi: 10.1016/j.jacc.2012.01.001. Epub Jan. 31, 2012. PMID: 22300974.
(Continued)

*Primary Examiner* — Thomas McEvoy
(74) *Attorney, Agent, or Firm* — The Webb Law Firm, P.C.

(57) ABSTRACT

A self-expandable stent includes a folded cylindrical sheet wall, which is folded along axes parallel to the longitudinal axis of the sheet of the cylindrical wall creating three or more drop shaped loops having an inner diameter and an end portion where the sheet of the cylindrical wall contacts each other along an contact surface parallel to the longitudinal axis, wherein each of the at least three bending loops are rotated towards the end portion of an adjacent loop, wherein the end portion has a curvature describing a bending diameter. The improvement includes providing a stent within a fold and deploy structure being able to exert sufficient
(Continued)

compression ratios as well as sufficient radial outward forces on the vessel wall, once deployed.

6 Claims, 12 Drawing Sheets

(52) U.S. Cl.
CPC ... *A61F 2230/005* (2013.01); *A61F 2250/001* (2013.01)

(56) References Cited

U.S. PATENT DOCUMENTS

| | | |
|---|---|---|
| 2008/0132996 A1 | 6/2008 | Drasler et al. |
| 2013/0090727 A1 | 4/2013 | Forster et al. |
| 2017/0065411 A1* | 3/2017 | Grundeman .......... A61F 2/2418 |

OTHER PUBLICATIONS

Mazilu et al., Self-Expanding Stent and Delivery System for Aortic Valve Replacement, J Med Device, 2012, pp. 410061-410069, vol. 6, No. 4, doi:10.1115/1.4007750.

* cited by examiner

SELF-EXPANDABLE STENT, METHOD AND DEVICE TO PRODUCE THE SELF-EXPANDABLE STENT

CROSS-REFERENCE TO RELATED APPLICATIONS

This application is the United States national phase of International Application No. PCT/EP2019/071346 filed Aug. 8, 2019, and claims priority to European Patent Application No. 18194304.4 filed Sep. 13, 2018, the disclosures of which are hereby incorporated by reference in their entirety.

BACKGROUND OF THE INVENTION

Field Of The Invention

The present invention relates to a self-expandable stent, a method and a device to produce the self-expandable stent, to compress the self-expanding structure into a delivering catheter, and a device therefor; especially provided in the context of transcatheter aortic valve replacements or short TAVR/TAVI.

Description of Related Art

D. Mazilu et al. have published an article relating to a "Self-expanding stent and delivery system for aortic valve placement" in Journal of Medical Devices, Vol. 6, 2012, describing self-expanding stent structures, methods and devices to compress the self-expanding structure for delivery.

D. Holmes Jr. et al. have published an "2012 ACCF/AATS/SCAI/STS expert consensus document on transcatheter aortic valve replacement" in the Journal of the American College of Cardiology, Vol. 59, No. 13 from 2012 with further elements relating thereto.

U.S. Pat. No. 6,165,210 discloses a self-expandable helical intravascular stent and stent-graft, which is not applicable in the present solution since the present solution provides symmetric stent extensions.

WO 95/26695 A2 discloses a self-expandable stent and stent-graft and method of using them, wherein the foldable stent or stent-graft can be delivered with or in a catheter or via other suitable techniques. The device is expanding or is unfolding using a torsional member aligned with a longitudinal access of the stent. The stent preferably has an undulating shape and can be helically deployed to form the generally cylindrical shape eventually deployed as the stent or it may be formed of one or more rings.

SUMMARY OF THE INVENTION

Based on this prior art it is an object of the present invention to improve the placement of a stent in a lumen using a transport catheter. It is a further object to improve the placement of a stent as part of a transcatheter aortic valve replacement.

The stent should have no wiry structure, no torsional undulating elements or similar element but mainly uniform cylindrical walls. In this context it is also an object to provide an improvement as a method of providing a stent within a fold and deploy structure being able to exert sufficient compression ratios as well as sufficient radial outward forces on the vessel wall, once deployed.

A self-expandable stent comprises a folded cylindrical sheet wall, which is folded along axes parallel to the longitudinal axis of the cylindrical sheet wall creating three or more drop shaped loops having an inner diameter and an end portion where the cylindrical sheet wall contacts each other along an contact surface parallel to the longitudinal axis, wherein each of the at least three bending loops are rotated towards the end portion of an adjacent loop, wherein the end portion has a curvature describing a bending diameter.

The invention provides a combination of a uniformly stiff linear elastic shell, void of any torsional or undulating members and without irreversible (plastic) deformation of the material, and a folding scheme, which gives the stent several additional advantages. The deployment procedure connected with this stent is designed in a way that it cannot overload the vessel, since it only deploys to its initial diameter and not further and it also does not spring back after deployment. Bonding and interface to the leaflets are drastically enhanced due to the fact that the bond happens on a uniform shell which also deforms uniformly.

The sheet wall can be made of a fiber-reinforced polymer material, i.e. is based on a purely elastic, but very stiff material. The material comprises a reinforcing portion (fiber) which provides stiffness and a supporting portion for the fibers (matrix) which is a polymer. An advantage is that the chemical composition of the supporting polymer (matrix) can be chosen to be biocompatible and furthermore enhances the bonding of polymeric leaflets through chemical compatibility. Prior art stents have their leaflets sewed to the stent, which can now be automated by simple gluing them. This lowers production cost drastically. The material is purely elastic which allows, because once the structure is folded, to store all the energy in its deformation which can be released by a self-deployment at the intended spot and there is no residual deformation.

Such a self-expandable stent can have at one side end three crown like extensions and three leaflets are attached each one along a bonding zone at the connection line of an associated crown like extension to create a transcatheter aortic valve replacement. For example, in other embodiments the polymeric leaflet shape is cast into the cylinder. Then the leaflets would be hidden inside the cylinder. The leaflets will have to have a bonding zone along the connection line as bonding length.

A method to produce such a self-expandable stent comprises the steps of:
  providing a cylindrical sheetwall;
  pushing at at least three inward pushing portions radially on the cylindrical sheetwall, until a corresponding number of drop shaped loops are produced, wherein adjacent portions of the sheet are contacting and closing each loop at a contact surface;
  rotating each of the loops around a longitudinal axis, wherein the center of each loop moves on an radius reducing involute until the sheet of the loop contacts the adjacent loop portion at the contact surface; and
  introducing the folded stent along its longitudinal axis into a cylindrical sleeve.

Here, the loops are rotated around a longitudinal axis which is not the same axis as the one from the unfolded cylinder. Within such a method the at least three inward pushing portions are chosen in identical angular distances one from the other around the circumference of the sheet of metal.

A folding rig to produce such a self-expandable stent with the above mentioned method comprises a base plate onto which a number of drop shaped folding pins are provided near the center, wherein each folding pin has a drop portion having the bending diameter, wherein the base plate comprises a number of involute shaped rails each associated to a folding pin and having one end of each rail provided near a concave portion of the associated folding pin, wherein one roller having the inner diameter and oriented along the longitudinal axis is positioned and movable in the associated rail.

Such a folding rig has the rollers linked together for a connected movement of the rollers from the outer end to the inner end of the associated rail.

A simple deployment device for the stent according to an embodiment of the invention comprises a cylindrical constraint sleeve connected to a first pulling wire on its distal end and a deployment plate connected to a second pulling wire on its distal end, wherein the stent is provided proximal to the deployment plate.

For an improved positioning of the stent, it is possible that the deployment device further comprises a base plate onto which a number of drop shaped folding pins are provided near the center on the proximal end and which base plate having a third pulling wire on its distal end, wherein each folding pin has a drop portion having the bending diameter, wherein the deployment plate has a number of through going openings complementary to the folding pins, wherein the deployment plate is positioned on the folding pins and wherein the stent is provided on the folding pins.

This latter mentioned deployment device provides for an intermediate deployment into a drop/star-like shape. However, when exiting its sleeve, the stent automatically goes into the intermediate state before touching the vessel walls and then deploys directly back to a cylindrical shape. However, such intermediate step can be used for a more accurate positioning.

Within the deployment device the third pulling wire is provided inside the second pulling wire having at least partly the form of a sleeve and the first pulling wire is provided around the second pulling wire having the form of at least part of a sleeve. This enables the pulling of the three different elements for an extraction of the stent from the deployment device.

A further possibility of actuating the deployment comprises a unit to pressurize pneumatically the area between the back wall of sleeve and deployment plate like a syringe or piston, which would automatically push out the stent out of the sleeve. Therefore, only one pulling wire has to be pressurized from the inside.

The deployment of the stent is based on stored elastic energy and provides a snap-through/back-effect for an irreversible deformation into the final stent configuration. The folding structure according to the invention provides two main advantages of deployment and deliverability. Required for the deployment is an intermediate folding stage that is smaller than the vessel with no tangling up. A requirement for deliverability is that the final stage has a reduced diameter, which is so drastically reduced without reaching the maximum allowed strain on the material. Said final folded stage has to be constrained to the diameter of the catheter for delivery.

It has been shown with different embodiments prepared by the applicant that a glass and carbon fibre reinforced polymer cylinder could reduce a diameter of the structure by 250% without failure of the material for a three or four loop folding. The structure, when provided smaller than the vessel, allows, when the device is releasing its energy, it pops up to its initial cylindrical geometry widening slightly any artery as lumen where there are in and will then result in a fixation force fixing the stent inside especially the said lumen and artery. This is possible since the artery walls are not a solid cylinder but a yielding and flexible wall which perfectly matches with the release of the potential energy stored in the folded stent deploying its essentially cylindrical form with its inherent possibility to lean against the adjacent lumen wall.

As is was shown by the experiments disclosed in the present specification, three-loop folding, four-loop folding and five-loop folding provide sufficient reduction of such a diameter although additional loop foldings, i.e. of higher order, are possible. A reduced effective diameter can already reached with three-folding structure but can be reduced even more by a four or five folding structure.

The folding efficiency in respect of the loop count could be shown to be increased drastically starting from the three folding structure up to the five holding structure, whereas additional loops as the six loop folding structure or seven loop folding structure does not improve the result as the additional loops from three to four or four to five.

It is an advantage of the present folding procedure, according to the invention, that the deployment principle comprises an inverse buckling problem. In other words, the structure is forced into an unstable state with its first folding stage, which provides a n-th mode of buckling under radial pressure, whereas n is the number of loops to be created.

Then, the linear elastic material behaviour provides the snapping effect, since, if the resulting contact pressure from stretching the artery is lower than the critical buckling pressure of the stent cylinder, the structure snaps back into the original state.

A further advantage arises by the environment where the stent is placed. It is usually a confined environment like an artery where the structure creates uniform radial pressure with a snap-through deployment as long as $RF_{artery} \times A_{artery} < P_{crit}$.

U.S. Pat. No. 6,165,210 provides a stent structure based on helix wiring with a stent-graft of soft material cellulose. The disclosure of the stent-graft to be folded in different ways, especially FIG. 13e of the prior art, shows exerting pressure on three areas 120° apart to create a three pointed star, which would then be turned as a spiral galaxy. However, this drawing shows the deformation of the helix wiring stent structure since the device is turned around centre with its prior art reference numeral 203 without any indication how this is achieved.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF THE INVENTION

FIG. 1 to FIG. 6 show subsequent steps of a method of folding a thin fibre reinforced cylinder stent 10 into a shape where the folded stent 10 is positioned inside a hollow introduction cylinder, usually a catheter, not shown in FIGS. 1 to 6.

Figures 1, 2, 3:
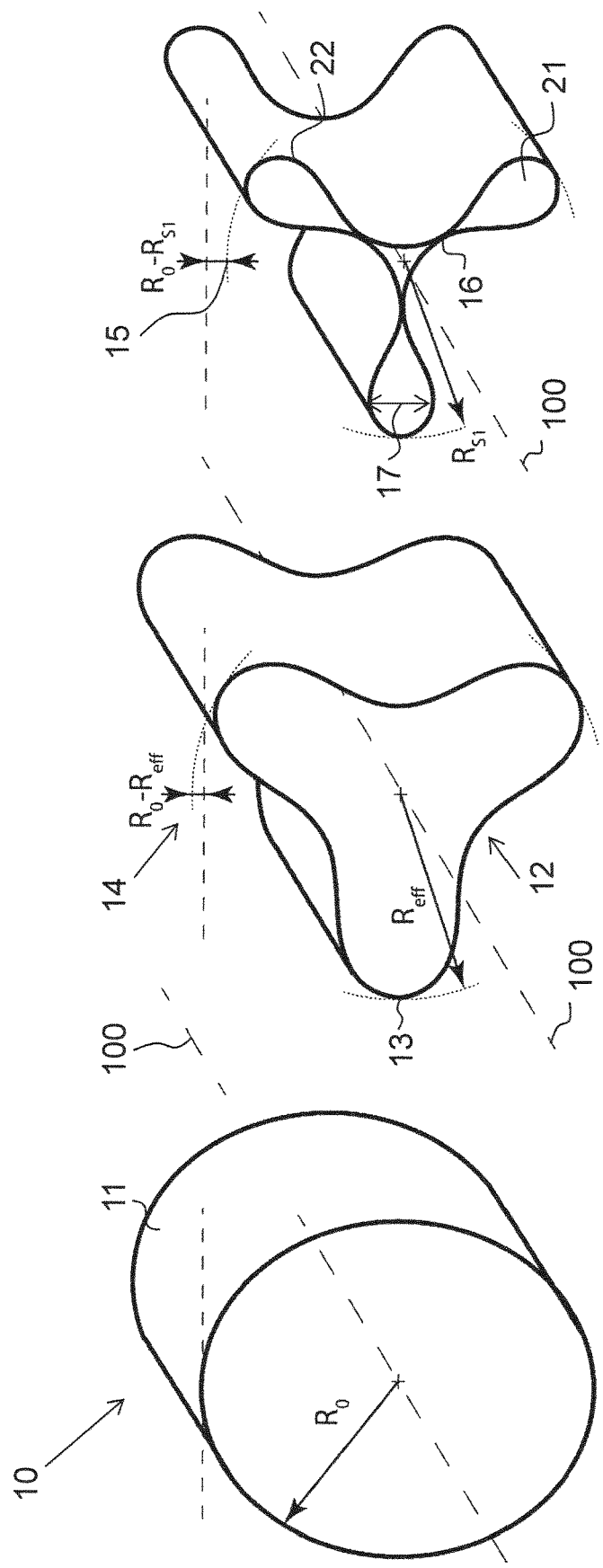
FIG. 1 shows a schematical perspective view of the starting point of a folding scheme of a thin fibre reinforced cylinder stent.
FIG. 2 shows a schematical perspective view of the first deformation step of the folding scheme of the stent from FIG. 1.
FIG. 3 shows a schematical perspective view of the second reduction step of the folding scheme of the stent from FIG. 1.

FIG. 1 shows a schematical perspective view of the starting point of a folding scheme of the thin fibre reinforced cylinder stent 10. Said stent 10 comprises a thin cylindrical wall 11 of radius $R_0$ along its longitudinal axis 100. The cylindrical sheet 11 is initially positioned centrally on a device, which will be described as an embodiment for executing the folding method as shown in connection with FIG. 14A and FIG. 14B.

FIG. 2 shows a schematical perspective view the first deformation step of the stent 10 starting from a configuration as shown in FIG. 1. Three areas are provided as inward pushing regions, wherein the cylindrical sheet 11 of stent 10 is pushed radially towards the longitudinal axis 100 and thus effectively reducing also the radius $R_{eff}$ of the outmost portions 13 of the cylinder. The dotted line of the outmost portion 13 forms at each point in time the effective cylinder diameter of the folded stent 10. This radius $R_{eff}$ is at the beginning of the process larger than the initial diameter $R_0$ as shown by the positive value of the difference $R_0-R_{eff}$. The inward pushing regions 12 are created by here three pins positioned in an angular distance of 120 degrees one from another and oriented in the direction of longitudinal axis 100. They are moving inwardly on a curve which can be a radial or a non-radial one.

FIG. 3 shows a schematical perspective view of the second reduction step of the folding scheme of the stent 10 from FIG. 1, following the first reduction step as shown in FIG. 2. Here, the inward pushing regions 12 have been pushed towards the central longitudinal axis 100 in a way that neighbouring inward pushed regions 12 are touching the adjacent inward pushed region at lines 16. The lines 16 are all in parallel to the longitudinal axis 100. It can be seen from FIG. 3 that the outmost portion 13 of the stent has now a smaller envelope with diameter $R_{S1}$, wherein $R_0-R_{S1}$ provides an intermediate reduction 15.

Here the three pins (not shown in FIG. 3) are quite near one to the other and allow the stent wall 11 to provide three hollow cavities 21 at the outmost portions 13 which have a small folding diameter 17 compared to $R_0$ and $R_{S1}$. The hollow cavities 21 create loops 22 which are subsequently bent as explained in connection with FIG. 4 to FIG. 6.

Figure 4:
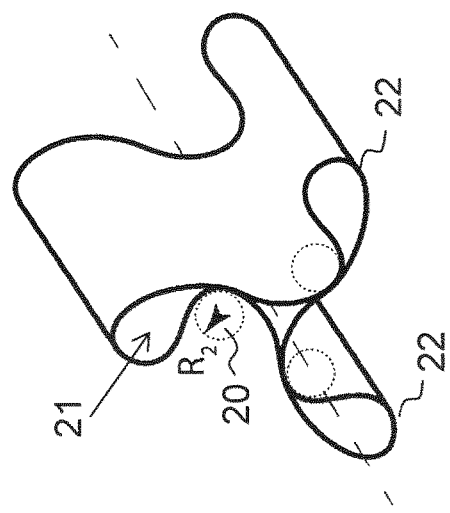
FIG. 4 shows a schematical perspective view of the starting movement of the twisting movement of the folding scheme of the stent from FIG. 1.

Summarizing the initial size reduction steps of FIG. 1 to FIG. 3, the cylinder of stent 10 is deformed by three point loads to the star like shape of FIG. 3. FIG. 4 now shows a schematical perspective view of the starting movement of a twisting movement of the folding scheme of the stent from FIG. 1. This resulting loop 22 from FIG. 3 is twisted around radei shown in FIG. 4 with dotted points as provided by bending cylinders 20 outside of the cylinders axis 100 to a resulting chiral structure. In this context, FIG. 4 shows the starting movement of the twisting movement, wherein the contact line 16 from FIG. 3 is contacting the middle of said bending cylinder 20 having a diameter $R_2$, which diameter is chosen to allow the necessary small curvature of the stent sheet 11 without going beyond, i.e. below, the bending diameter limits, which are chosen to be smaller than said $R_2$.

The rotation of the three loops 22 having each said internal cavity 21 is executed via pins within these internal cavities 21. These three turning portions rotate around the axis 100 with a decreasing distance from said axis 100. The internal cavities 21 of loops 22 have and maintain a diameter, which is of course not smaller than said $R_2$. FIG. 4 shows a rotation of these regions around the internal cavity 21 in a counter clockwise direction, wherein this movement is counter-clockwise in relation to the position or movement of the bending cylinders 20.

Figure 6:
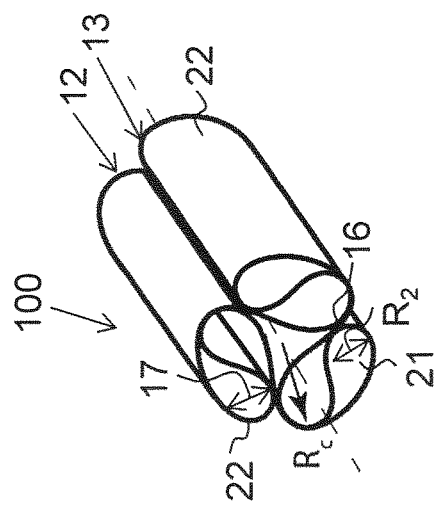
FIG. 6 shows a schematical perspective view of the final portion of the folding step of this procedure applied to the stent as shown in FIG. 1.
Figure 5:
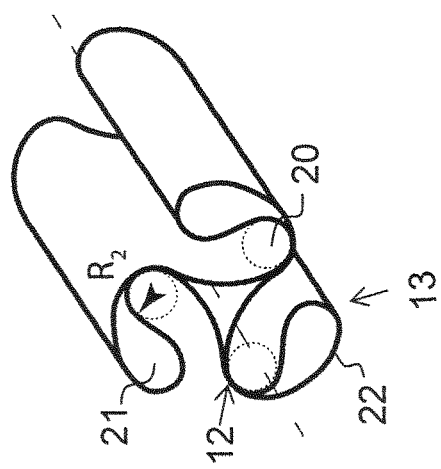
FIG. 5 shows a schematical perspective view of the ongoing folding step of this procedure applied to the stent as shown in FIG. 1.

FIG. 5 shows the ongoing folding step within this procedure, wherein the outer portion with the cavity 21 is wound in a contacting manner around the mentioned bending cylinder 20. Therefore, the folded portions approach the neighbouring contact line 16 and reach them in the final position of the folded stent 10 as shown in FIG. 6. There, the bending cylinder 20 is just providing an outer limit of the pivotate valve, whereas the turned inward pushing regions 12 are contacting the adjacent outmost portions 13. As FIG. 6 shows a schematical perspective view of the final folding step of this procedure applied to the stent 10, the enveloping diameter Rc of the folded stent 10 is smaller than the initial diameter Ro.

The folded stent 10 is in its folded state introduced in a catheter to be positioned in the intended lumen of the body. Then the folded stent 10 is longitudinally pushed outside said catheter to be positioned inside the lumen where it unfolds as explained later on.

Figure 7:
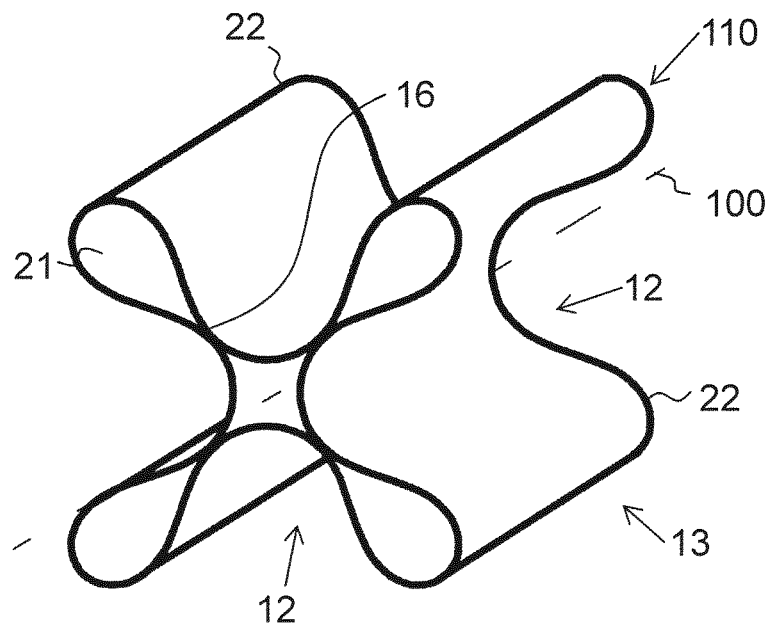
FIG. 7 shows a schematical perspective view of the second reduction step of the folding scheme of a stent according to an embodiment with four inward pushing regions.
Figure 8:
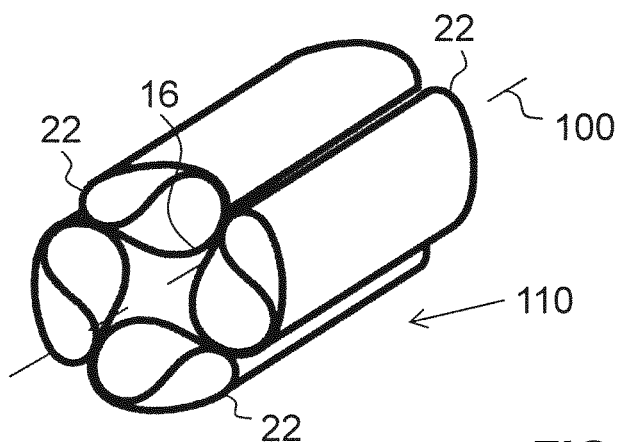
FIG. 8 shows a schematical perspective view of the final folding step of this procedure applied to the stent as shown in FIG. 7.

FIG. 7 shows a schematical perspective view of the second reduction step of the folding scheme of a stent 110 according to an embodiment with four inward pushing regions 12. Same features of different embodiments receive identical reference numerals. These four inward pushing regions 12 are provided in an angular distance of about 90° one from the other, so that also for internal cavities 21 are created, which, when the structure is rotated around the longitudinal axis 100 around bending cylinders similar to the cylinders 20 ensure a minimum turning radius. Said radius has to be seen in connection with FIG. 8 showing a schematical perspective view of the final folding step of this procedure applied to the stent 110 as shown in FIG. 7. There, each of the four bending portions being loops 22 contacts the adjacent contact line 16, wherein the movement of the loops 22 is counter-clockwise in relation to the position or movement of the bending cylinders 20.

Figure 9:
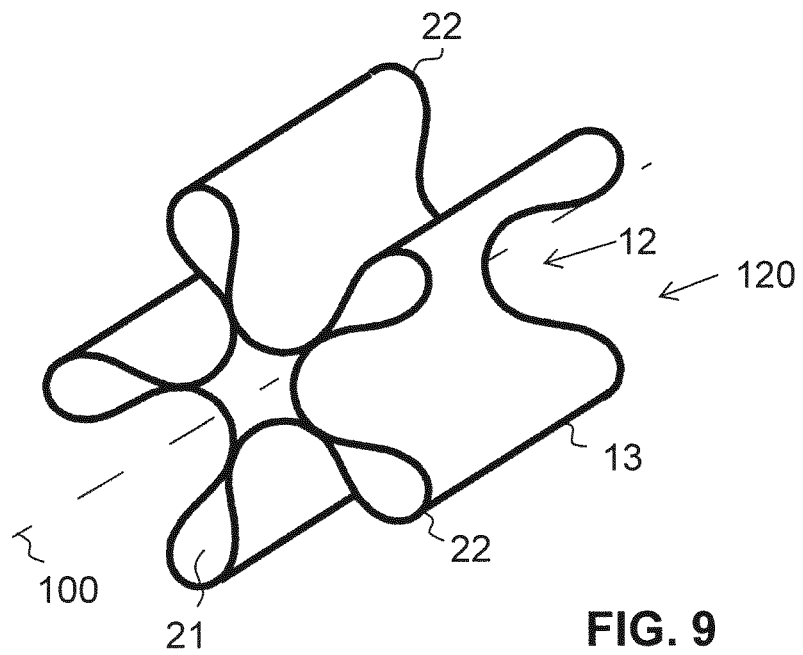
FIG. 9 shows a schematical perspective view of the second reduction step of the folding scheme of a stent according to a further embodiment with five inward pushing regions.
Figure 10:
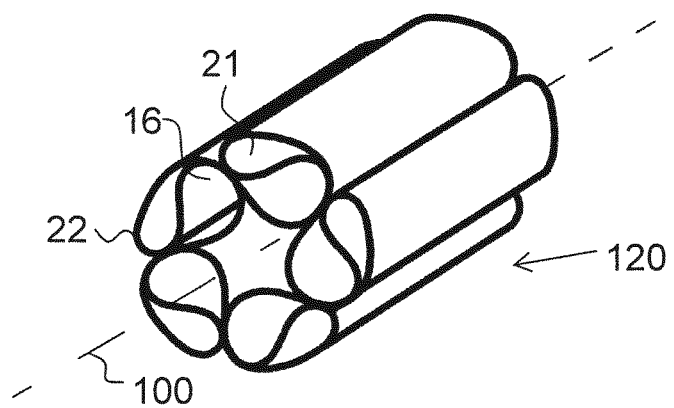
FIG. 10 shows a schematical perspective view of the final folding step of this procedure applied to the stent as shown in FIG. 9.

FIG. 9 shows a schematical perspective view of the second reduction step of the folding scheme of an embodiment of a stent 120 with five folding loops 22. FIG. 10 shows a schematical perspective view of the final folding step of this procedure applied to the stent 120 as shown in FIG. 9. Same features have received the same reference numerals for the same functional approach. Here, five bending cylinders (not shown in FIG. 9) are provided, which then turn the loops 22 against the adjacent intermediate section with the contact line 16 and reach an outer diameter which is quite smaller than the original cylindrical portion of the stent 120.

Figure 11:
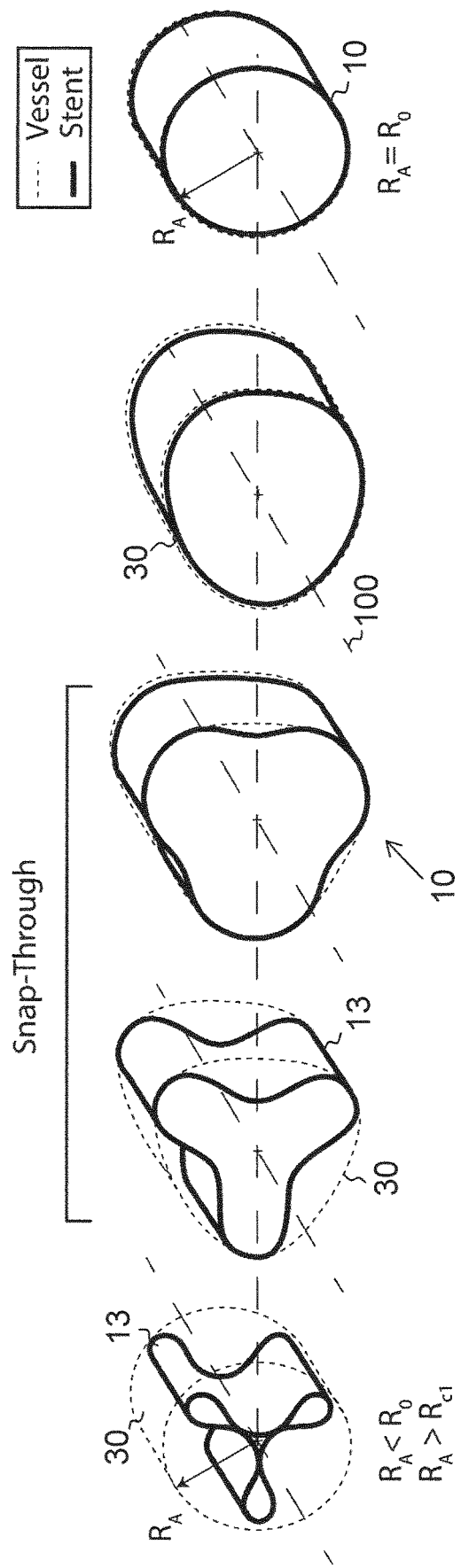
FIG. 11A to 11E show the inverse folding process when the stent folded as shown in FIG. 6 is released inside the intended device.

FIG. 11A to FIG. 11E show the inverse folding process when the stent 10 of FIG. 6 is released inside the application device, i.e. a catheter, wherein the starting image of FIG. 11A reflects the situation of stent 10 according to FIG. 3. In other words, starting from the introduction size of the folded stent 10 of the drawing of FIG. 6, an uncaged stent 10 from an encasing holding structure initially resolves the position of the bent loops 22 and pushes the outmost portions 13 against the surrounding vessel surface 30, which is also shown as a simple cylindrical structure. Here, it has to be noted, that these vessel surfaces 30 are living material of a patient and are usually not mathematically correct hollow cylinders but have imperfections as recesses and protrusions within the inner lumen, wherein at the beginning of the defolding process the folded stent 10 just touches the vessel surface 30 at these three regions 13 as shown in FIG. 11A and FIG. 11B. When the inward pushed regions 12 are moving outwardly away from the longitudinal axis 100, they provide as shown in FIG. 11B and FIG. 11C a snap-through effect occurs, wherein the stored energy stored as potential energy within the folded structure is released and allow the inward portions 12 to be pushed outward and to engage the surface of the vessel 30 of the patient in the way as shown in FIG. 11D. FIG. 11D shows the expanded stent 10 in the vessel and since the vessel surface 30 is not a perfect cylinder, the stent has taken the form of the vessel modulo its extension strength and tries to move the vessel to the most preferred symmetrical stent formation as shown in FIG. 11E, where the outer diameter $R_a$ of the vessel 30 is identical to the outer diameter $R_0$ of the stent 10.

Figure 12:
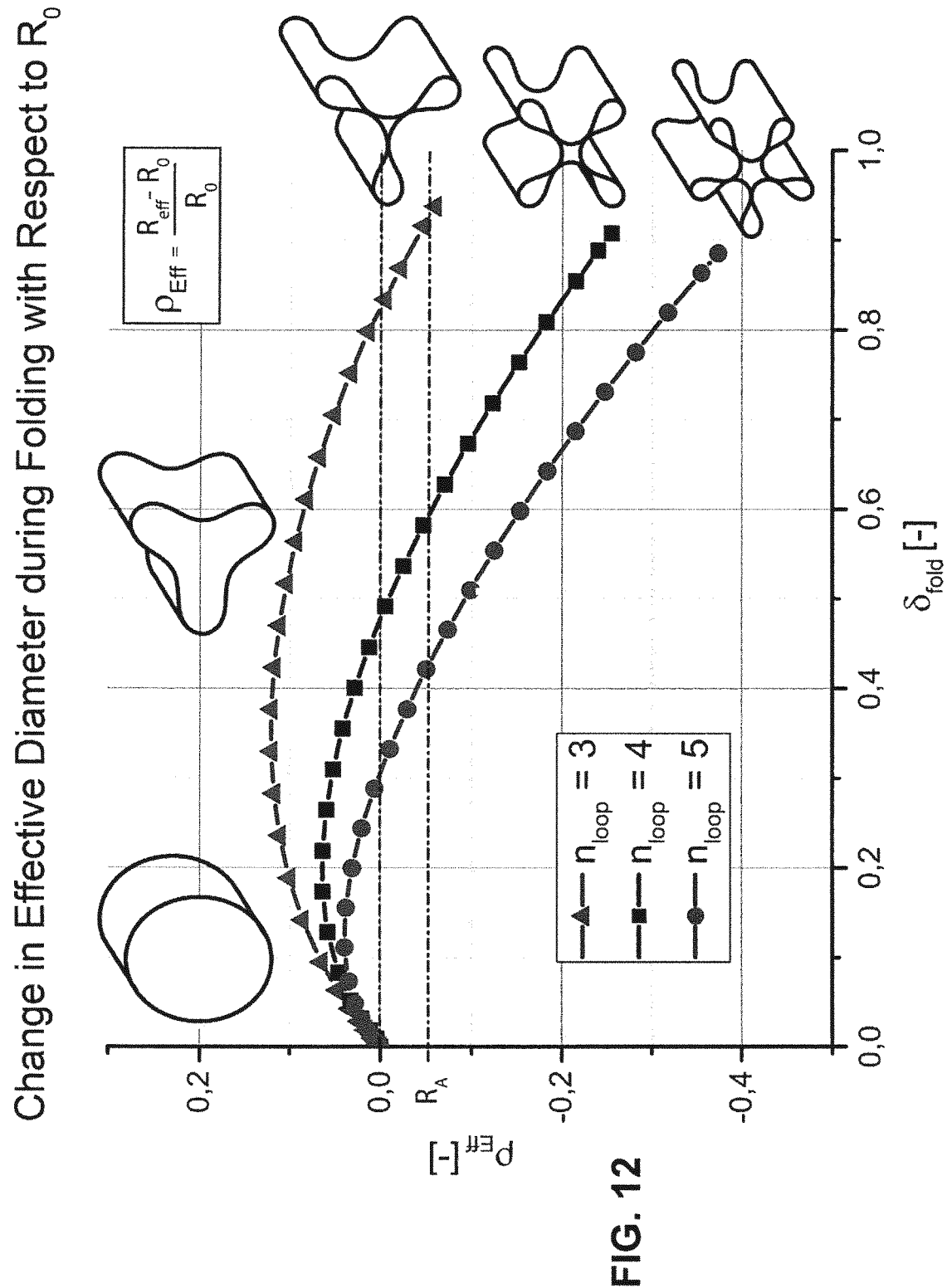
FIG. 12 shows a diagram with three curves of the effective diameter though infolding with respect to the initial diameter $R_0$ for three folding loops, four folding loops as well as five folding loops.

FIG. 12 shows a diagram with curves reflecting the change in effective diameter $\rho_{Eff}$ against the folding progress $\delta_{fold}$ between 0 (stent 10 unfolded) and 1 (stent fully folded). The curve made up of triangles show the development of the initial diameter $R_0$ for the three folding loop, the curve with the rectangles show the fourth folding loop and the third curve with full circles shows the embodiment with five circular loops. Starting from an effective identical diameter $R_{eff}=R_0$, and thus $\rho_{Eff}=(R_{eff}-R_0)/R_0=0$, the initial bending steps temporarily increase the diameter of the stent 10, 110, 120 but then reduces the effective diameter far below the original diameter especially for the higher graded loops, wherein the third degree loop reaches just the value $R_a$ before unfolding. It is mandatory that the stent 10, 110, 120, when the final folding step of the procedure was executed, reaches a diameter smaller than $R_a$ to be positioned in a positioning device as a catheter having an outer diameter of $R_a$ plus the thickness of the wall of the catheter.

Figure 13:
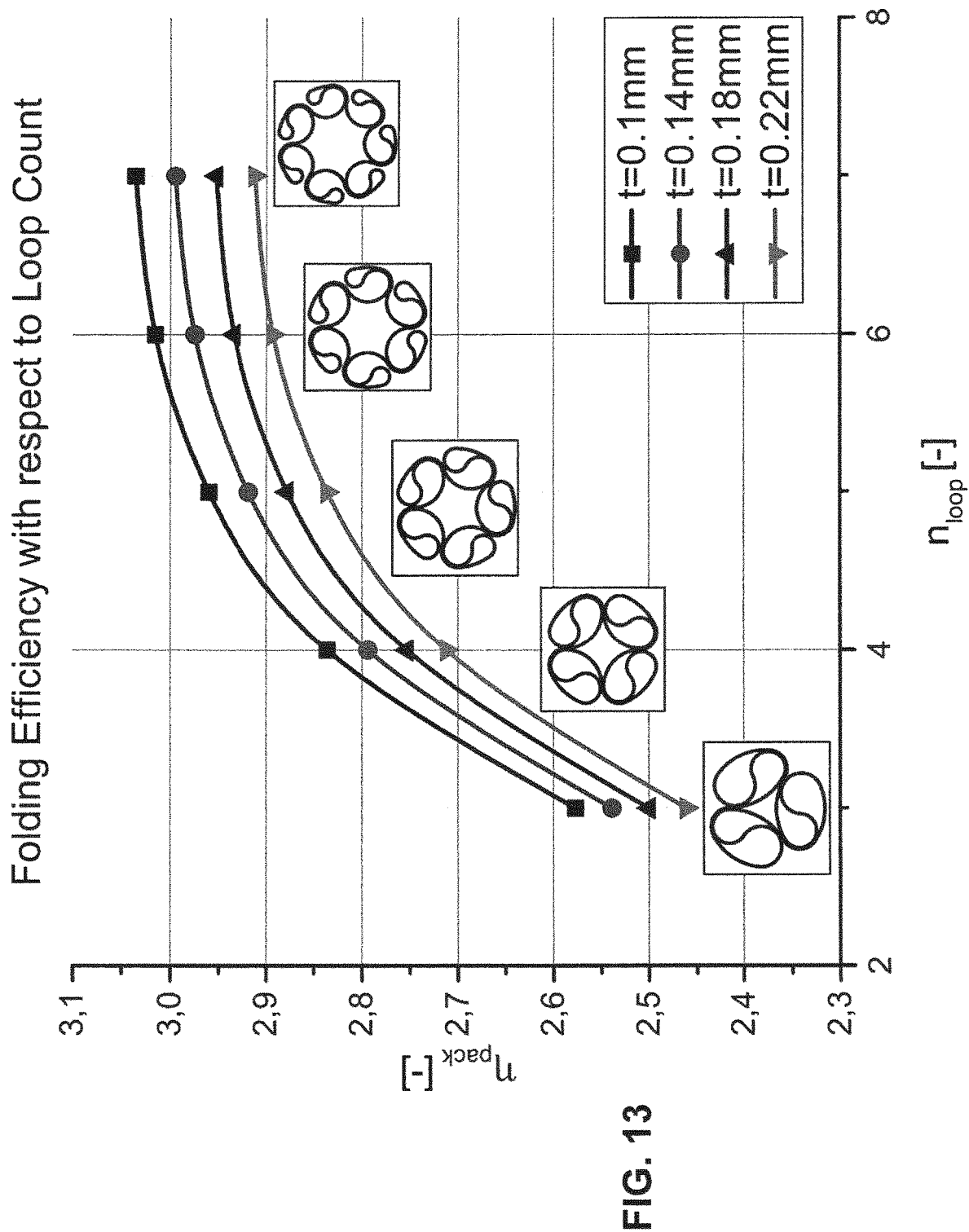
FIG. 13 shows a diagram of the folding efficiency in view of the loop count, which is shown for loops from 3 to 7 with different diameter thickness of the stent material.

FIG. 13 shows curves relating to the folding efficiency in view of the loop count, which is shown for loops from 3 to 7 with different diameter thickness t of the stent material, starting from t=0.1 mm shown as filled squares, t=0.14 mm with full circles, t=0.18 mm for triangles with the tip upwards and finally the thickest stent material t=0.22 mm shown as triangles with the tip downwards, show that the main advantage of the packing compression can be obtained by not choosing a three prong folding approach but a four or five prong folding approach, whereas higher level approaches as six or seven loops do not provide a further greatly improved device, since the packing ratio $\eta_{pack}=R_0/R_c$ reaches for all thicknesses of the stent material values $\eta_{pack}$ about 2.7 to 2.9 for four loop counts.

Figure 14A:
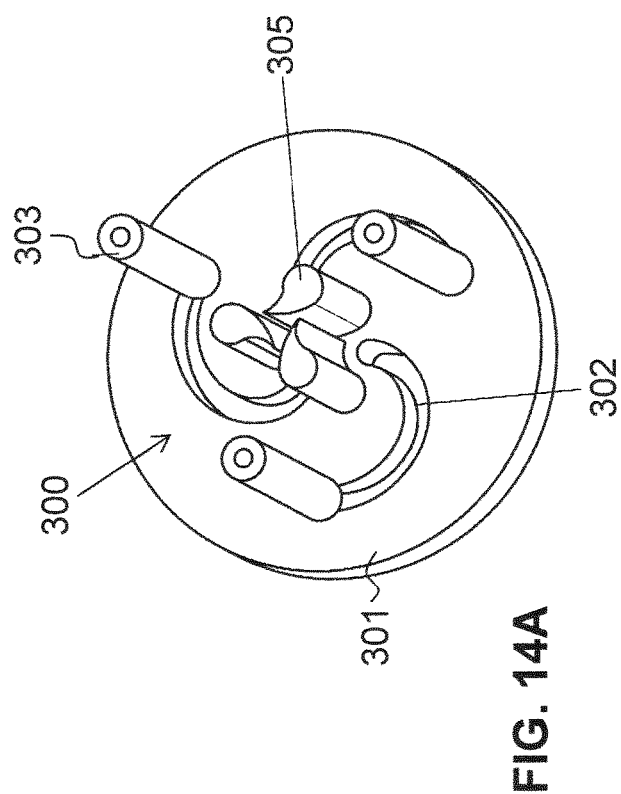
FIG. 14A and 14B show a schematical perspective views of a folding rig for the stent of FIG. 1 without and with a positioned stent, respectively.
Figure 14B:
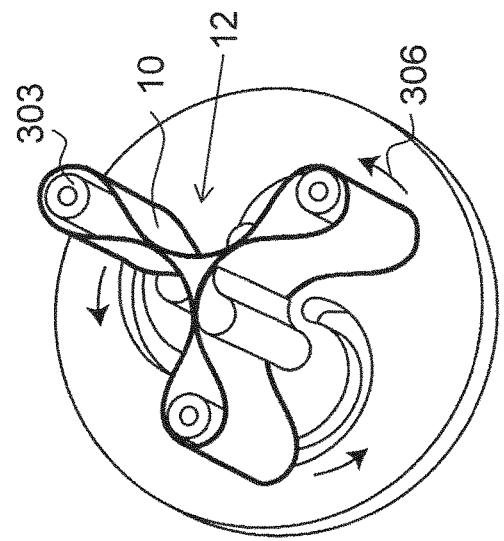
Figure 15A:
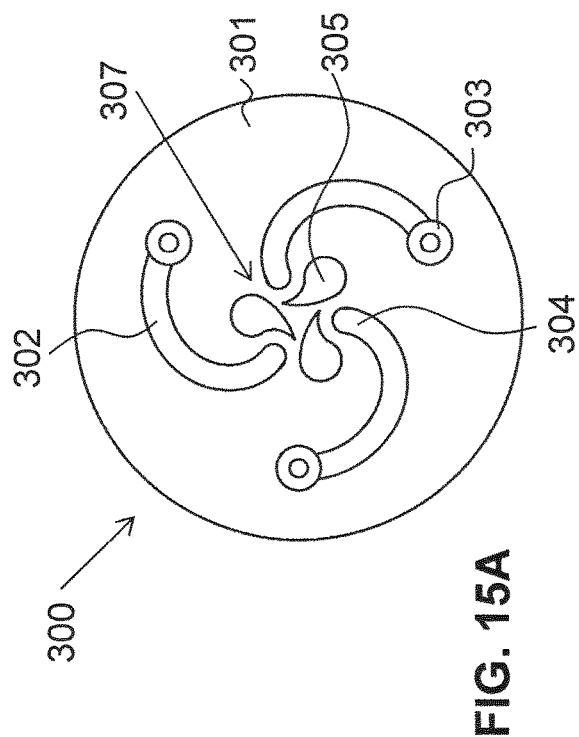
FIG. 15A and 15B show a view form above on the folding rig of FIG. 14A and 14B, respectively.
Figure 15B:
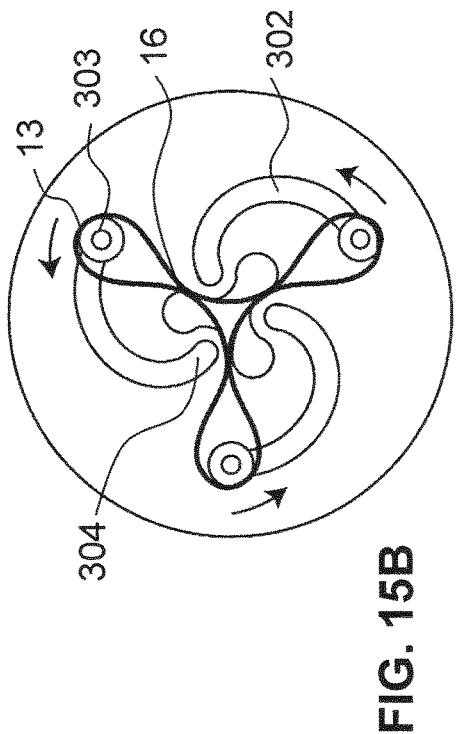

FIG. 14A shows a schematical perspective view of a folding rig 300 for the self-expandable stent 10 of FIG. 1 without a positioned stent, whereas FIG. 14B shows the same folding rig 300 with a partially positioned stent 10. These figures are described in connection with FIG. 15A and 15B each showing a view form above on the folding rig 300 of FIG. 14A and 14B, respectively. The folding rig 300 comprises a base plate 301, which has three involute shaped rails 302. The number of rails 302 follows the folding number, here three, but can be four, five or more in other embodiments. The envolute shaped rails 302 provide guidance for three folding pins 305 which can be amovibly attached to the folding plate 301 and (if needed) later removed to be used in the deployment device 400. The folding pins 305 prescribe a predetermined radius onto the stent structure to prevent overloading during folding. The folding happens due to the rollers 303 following the guidance rails 302, wrapping the lobes or loop 22 around the folding pins 305. The rollers 303 diameter is chosen to also prescribe a given radius onto the stent 10 at the lobe tip, to prevent overloading. The rollers 303 diameter ensure the predetermined minimum radius of internal cavity 21. The folding pins 305 are drop shaped with the tip oriented tangentially on the inside of the rig 300 and the circular rounded end being directed to the outer part of the rig and between the inner ends 304 of the envolute shaped rails 302, while a concave portion of the drop formed pin 305 is essentially complementary to the outer diameter of the roller 303 when it abuts at the inner end 304 of the rail 302, providing the contact of one outmost portion 13 of the stent 10 with the contact line of the adjacent portion 13. When fully wrapped, a catheter 450 as constraint can be placed around the wrapped structure and the folding rig 300 can be removed. Rollers 303 are shown in FIG. 14A, 14B, 15A and 15B positioned at the outer end of rails 302 opposite to the inner end 304 and are moved in the folding action according to arrows 306. It is noted that the initial placement of the stent 10 with the inward pushing regions 12 as shown in FIG. 14B is provided by manually positioning the stent sheet in between the space 307 between the folding pins 305.

Figure 16:
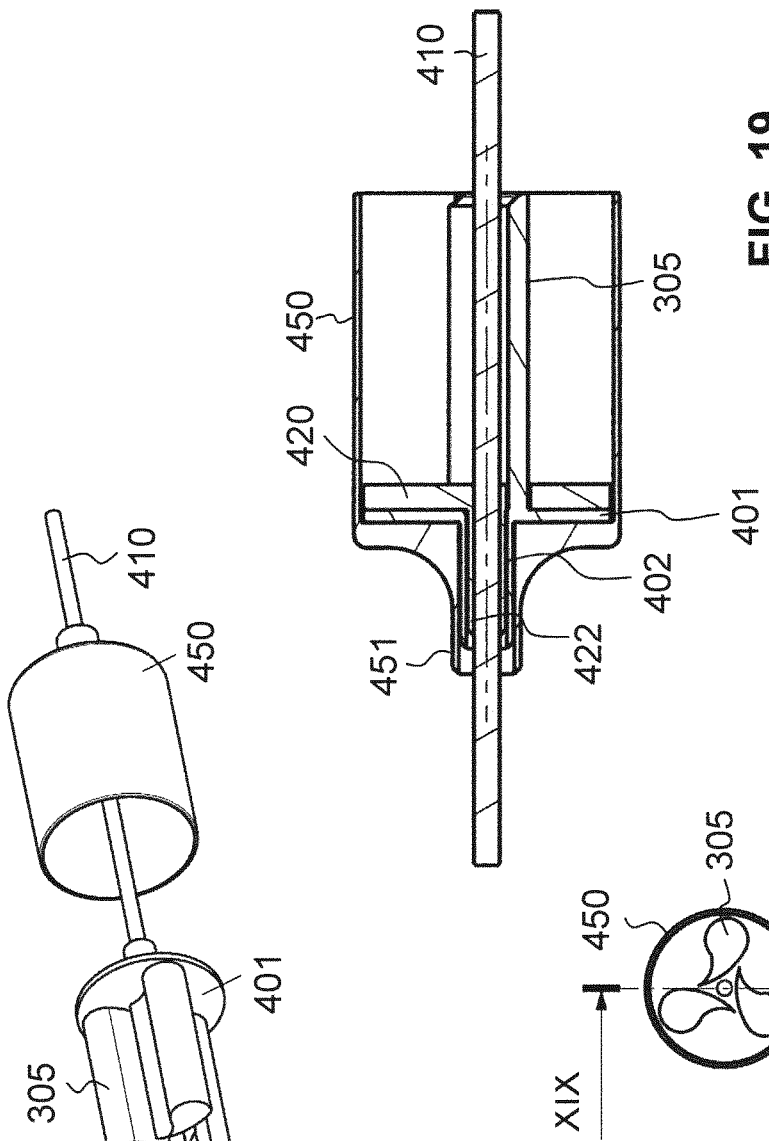
FIG. 16 shows a schematical exploded perspective view of a deployment device for the stent according to FIG. 1.
Figure 18:
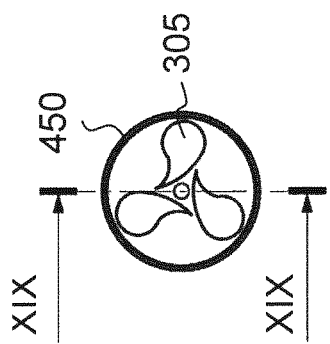
FIG. 18 shows a front view on the deployment device according to FIG. 16.
Figure 17:
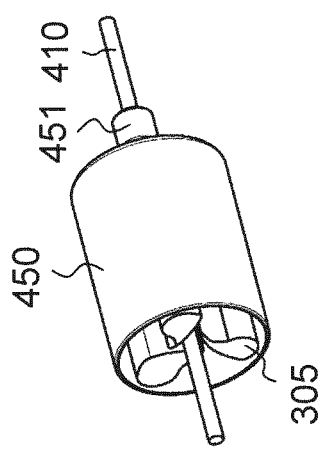
FIG. 17 shows a schematical perspective view of the deployment device of FIG. 16.
Figure 19:
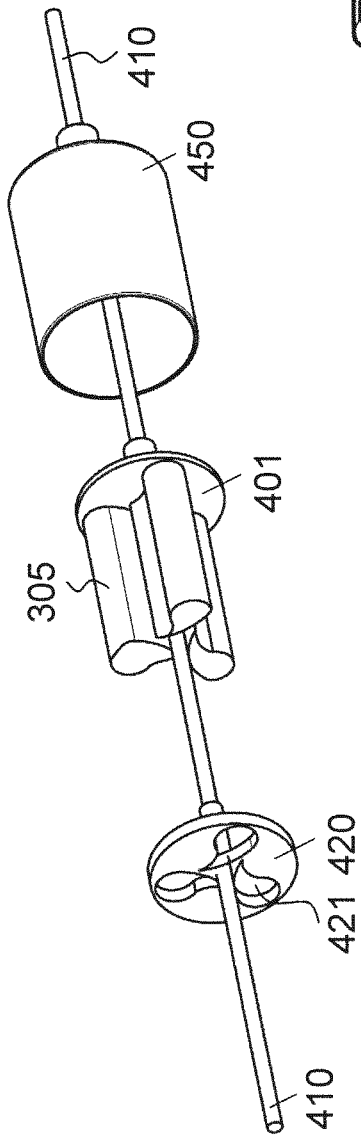
FIG. 19 shows a cross section view of the deployment device according to lines XIX-XIX in FIG. 18.

FIG. 16 shows a schematical exploded perspective view of a deployment device 400 for the stent 10 according to FIG. 1 comprising the catheter constraint 450. FIG. 16 can be better explained in connection with FIG. 17 showing a schematical perspective view of the deployment device of FIG. 16, FIG. 18 showing a front view on the deployment device 400 according to FIG. 16 and FIG. 19 showing a cross section view of the deployment device 400 according to lines XIX-XIX in FIG. 18.

The deployment device 400 according to an embodiment of the invention, which is able to achieve a two stage deployment (with intermediate shape), is a catheter device and comprises a catheter delivery wire (compared to regular TAVI systems) 410 which allows the delivering of the stent 10 delivery device 400 to the intended deployment spot. As already mentioned above, other embodiments of deployment device do not comprise an intermediate stage because the twisted loops unfold quick enough so the stent automatically reaches the intermediate stage before touching the artery walls. However it might be useful for better positioning and can therefore the two stage deployment (with intermediate shape) is described as an deployment alternative in the following description.

A cylindrical constraint 450 is part of the catheter, which constrains the folded stent 10 and keeps it packaged until the stent 10 is at its intended spot. Three folding pins 305 ensure the intermediate shape, once the hollow constraint catheter 450 is removed. The folding pins 305 can have and preferably will have an identical form to pins 305 of the folding rig 300. The folding pins 305 are positioned on a base plate 401 fitting inside the hollow constraint 450. Space 307 from the folding rig 300 is identically provided here between the pins 305 and the catheter delivery wire 410 is passing through a hole in base plate 401. Between the plate 401 of the folding pins 305 and the folded stent 10 is provided a deployment plate 420. Deployment plate 420 comprises three through holes 421 having the form of the folding pins 305. The number and form of the through holes 421 is chosen following the number and distribution of folding pins 305 to obtain a stent according to FIG. 1, FIG. 8, FIG. 10 or the higher loop number embodiments as shown schematically in FIG. 13. The deployment plate 420 has essentially the same diameter as plate 401 and is thus capable to be inserted opposite to plate 401 into the constraint catheter 450.

The task of this deployment plate 420 is to push the stent 10 out of the folding pin 305 structure on plate 401 to fully deploy, i.e. to follow the procedure as shown in FIG. 11A to FIG. 11E. This happens when the deployment device 400 with all parts is pulled away from the deployment spot. The three parts 420, 401 with pins 305 and hollow catheter 450 all have their own pulling wires, which are not specifically shown in FIG. 16 to FIG. 18 but explained in connection with FIG. 19, which shows a cross section view of the deployment device according to lines XIX-XIX in FIG. 18. Hollow catheter 450 is connected with the catheter constraint pulling wire portion 451; base plate 401 is connected with base plate retracting wire portion 402 which is provided surrounding catheter constraint pulling wire portion 451; and deployment plate 420 is connected with deployment plate pulling wire 422 which is provided surrounding the catheter constraint pulling wire portion 451 near the catheter cylinder 450. Of course, the order of these pulling elements can be changed. They are encapsulating the catheter wire 410 and each other. This allows an independent pulling of the single devices: first catheter constraint 450, then baseplate 401 with folding pins 305, and finally the stent sheet with holding plate 420 which allows the stage wise deployment which is depicted in FIG. 20.

Figures 20A, 20B:
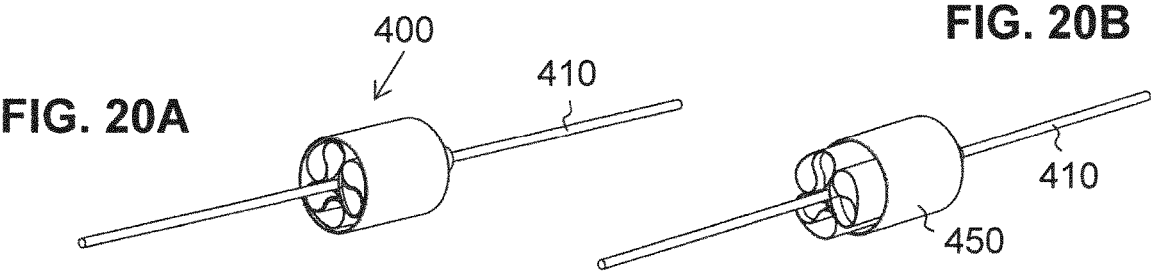
FIG. 20A to FIG. 20E show schematical perspective views of the method employing the deployment device of FIG. 16 to unfold the stent of FIG. 1.
Figures 20C, 20D:
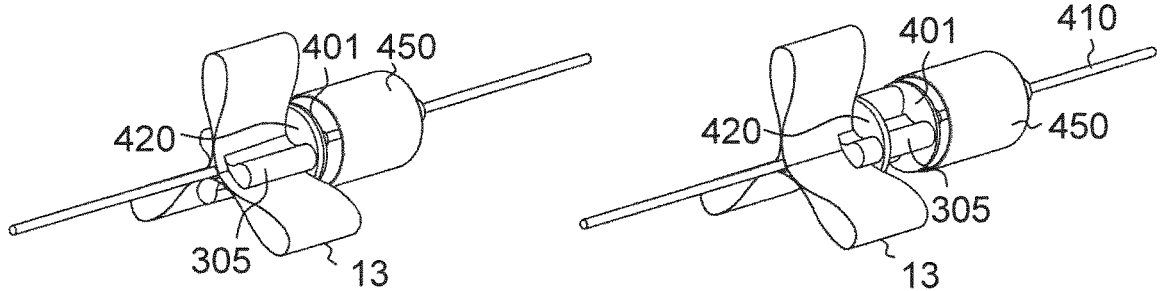
Figure 20E:
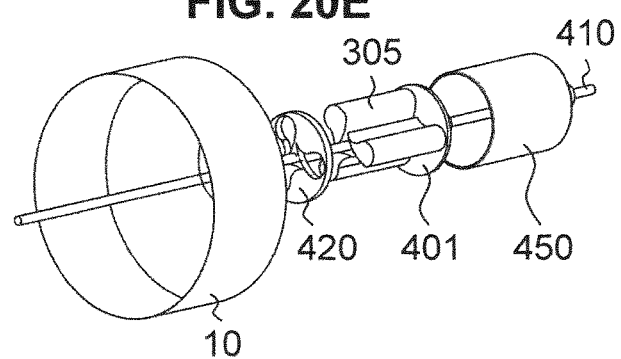

FIG. 20A to FIG. 20E show schematical perspective views of the method employing the deployment device 400 of FIG. 16 to unfold the stent 10 of FIG. 1. FIG. 20A shows step I, wherein the folded stent 10 inside the deployment device 400 is pushed to the intended deployment spot with the catheter wire 410. Here the same insertion like regular TAVI stents is applied. FIG. 20B shows step II, wherein the cylindrical catheter constraint 450 is removed by pulling it through wire 450 away from the heart. The wire 451 surrounding the catheter wire 410 is not shown in the figures. FIG. 20C shows step III, wherein, once the catheter constraint 450 is removed, stent 10 deploys to its intermediate shape, which is a configuration which is also shown in FIG. 11A. The outmost portions 13 of stent 10 abut against the inner wall of the lumen, where the deployment device 400 is placed. The wall of the lumen is not shown in FIG. 20A to FIG. 20E. FIG. 20D then shows step IV, wherein the base plate 401 is retracted, especially while the catheter constraint 450 remains in place. Then base plate 401 is retracted into the catheter constraint 450 for later removal. Base plate 401 is pulled away from the heart, resulting in deployment plate 420, which stays in place since the relating deployment plate pulling wire 22 is not actioned, pushing the intermediate stage stent 10 out of base plate 401. Finally, FIG. 20E shows step V, wherein stent 10 deploys and creates a radial outward force contacting the neighbor tissues. The passage from step IV to step V is shown in FIG. 11A to FIG. 11E. A specific leaflet and pertrusion, which are possible while providing transcatheter aortic valve implantation, are not drawn for simplicity. After the deployment procedure, the catheter elements hollow cylinder 450, base plate 401 with (un)folding pins 305 as well as deployment plate 420 are removed out of the artery by pulling them.

A further possibility of actuating the deployment comprises a pressure delivering unit to pressurize pneumatically the area between sleeve 450 and deployment plate 420 like a syringe or piston, which automatically pushes out the stent out of the sleeve 450. Therefore, only one pulling wire is necessary to retract the sleeve 450, whereas a pressure delivering unit is expanding the cavity between the back wall of sleeve 450 and the deployment plate 420.

Figure 21B:
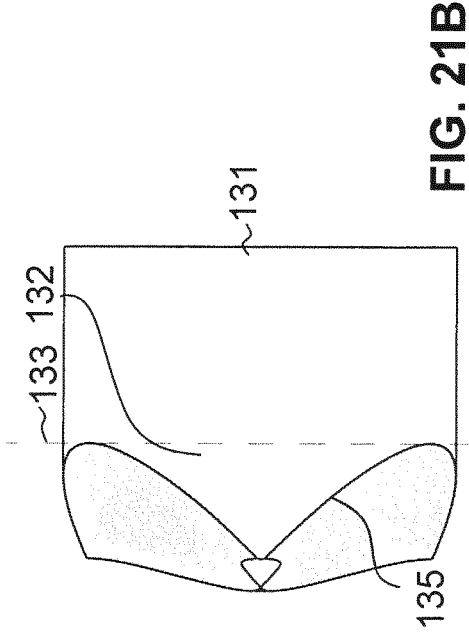
FIG. 21A and FIG. 21B show a perspective view and a side view of an embodiment of a composite stent with leaflets, respectively.
Figure 21A:
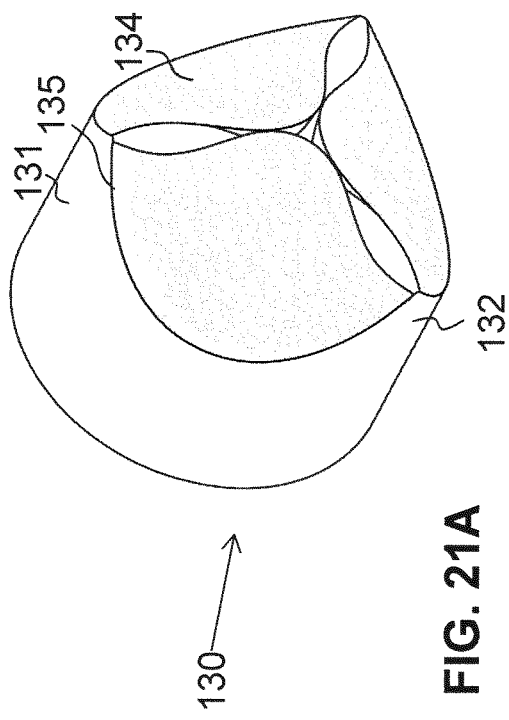

Since, in the case of transcatheter aortic valve implantation, the stent 10 is not just a hollow cylinder which expands, FIG. 21A and FIG. 21B show an embodiment of a composite stent 130 with leaflets 134, wherein FIG. 21A shows a perspective view and FIG. 21B a side view. The stent 130 then will comprise the main sheet wall 131, which is the folded cylinder. The folded cylinder will preferably have a crown-like extension 132, which is also a part of the cylindrical shell 131 and can be manufactured e.g with laser cutting. The crown-like extension 132 is the portion of the material of the cylindrical shell 131 beyond a front end line of the cylinder wall and acts as an interface to the three leaflets 134, which will be bonded onto the crown-like extensions 132 along the connection line 135. The bonding will most likely happen with either gluing, a direct casting procedure or 3D-printing.

Figure 22B:
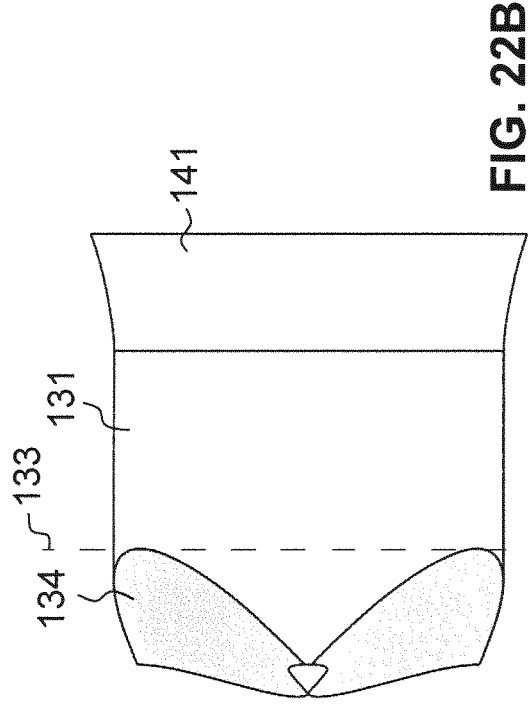
FIG. 22A and FIG. 22B show a perspective view and a side view of an embodiment of a composite stent with leaflets and a widening extension to a larger diameter.
Figure 22A:
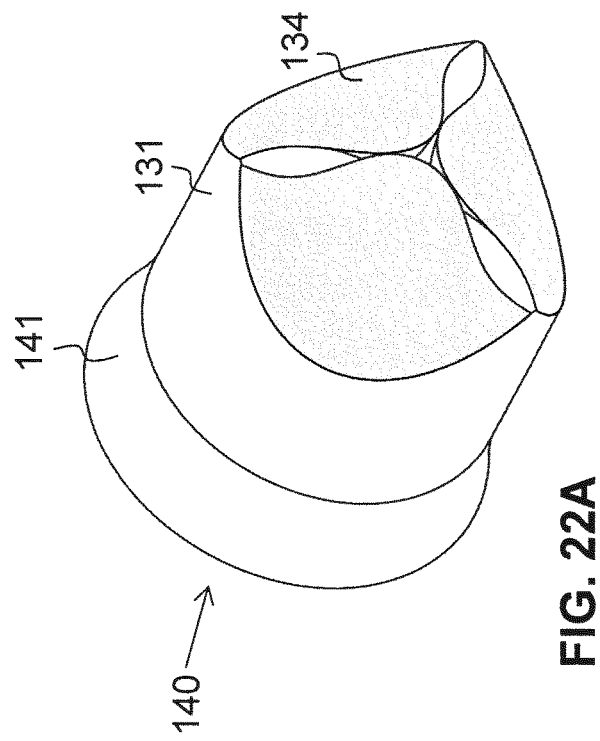

FIG. 22A and FIG. 22B show a further embodiment of a composite stent 140 with leaflets 134 and as a variation wherein the cylindrical main part 131 has a widening extension 141 to a larger diameter, which improves the frictional forces as well as produce a better fit in the artery which can be folded in the same way as the stent wall if the bending allows for the additional material to be stored within the same cavity room of the sleeve 45.

Figure 23:
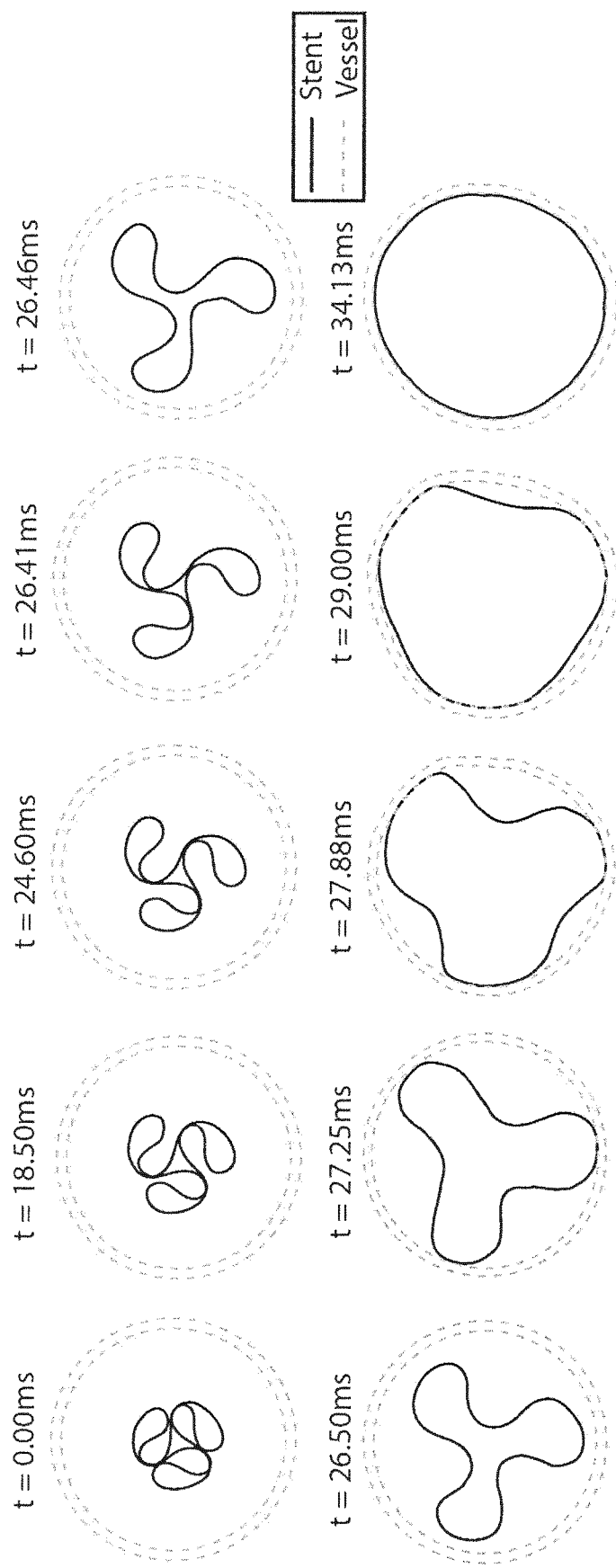
FIG. 23 shows the digitally drawn images of footage showing the deployment in an experiment with a highspeed camera of a stent according to an embodiment of the invention.

FIG. 23 show ten digitally drawn images of footage showing the deployment in an experiment with a highspeed camera of a stent according to an embodiment of the invention starting from t=0 milliseconds for the upper left drawing to t=34.13 milliseconds for the lower right image. The stent is always shown as a solid line whereas the vessel is shown as two concentric dotted lines. The images are in line with the drawings of FIG. 11A to FIG. 11E. The deployment was made with a single-step deployment device 400, i.e. without use of a base plate 401.

The invention claimed is:

1. A self-expandable stent comprising:
a cylindrical sheet wall having a longitudinal axis,
wherein the cylindrical sheet wall is folded around three or more longitudinal folding axes parallel to the longitudinal axis of the cylindrical sheet wall creating one drop shaped loop around of and for each of the folding axes,
wherein each drop shaped loop has an inner diameter, a starting portion of a drop shape with two cylindrical sheet wall portions in contact with each other creating a contact surface, and an end portion,
wherein each drop shaped loop is rotated towards the starting portion of an adjacent drop shaped loop,
wherein the end portion of each drop shaped loop has a curvature describing a bending diameter,
wherein a cylindrical sheet wall portion of each drop shaped loop contacts an adjacent cylindrical sheet wall portion of the starting portion of the adjacent drop shaped loop at
the contact surface of the adjacent drop shaped loop parallel to the folding longitudinal axis.

2. The self-expandable stent of claim 1, wherein the stent comprises a side end in the direction of the longitudinal axis, a predetermined number of crown like extensions having a connection line in direction of the side end, and a same predetermined number of leaflets, and
wherein the crown like extensions are provided at the side end, and each leaflet is attached along a bonding area at the connection line of an associated crown like extension.

3. The self-expandable stent of claim 2, wherein the predetermined number is three.

4. The self-expandable stent of claim 1, wherein the cylindrical sheet wall is made of a fiber-reinforced polymer material.

5. A method for producing a self-expandable stent comprising a cylindrical sheet wall having a longitudinal axis, wherein the cylindrical sheet wall is folded around three or more longitudinal folding axes parallel to the longitudinal axis of the cylindrical sheet wall creating one drop shaped loop around of and for each of the folding axes, wherein each drop shaped loop has an inner diameter, a starting portion of a drop shape with two cylindrical sheet wall portions in contact with each other creating a contact surface, and an end portion wherein each drop shaped loop is rotated towards the starting portion of an adjacent drop shaped loop, wherein the end portion of each drop shaped loop has a curvature describing a bending diameter, the method comprising the steps of:
providing a cylindrical sheet wall;
pushing at least three inward pushing portions radially on the cylindrical sheet wall until a corresponding number of drop shaped loops are produced;
rotating each of the drop shaped loops around a longitudinal folding axis parallel to the longitudinal axis of the cylindrical sheet wall, wherein the center of each drop shaped loop moves on an radius reducing involute until a cylindrical sheet wall portion of each drop shaped loop contacts an adjacent cylindrical sheet wall portion of the starting portion of the adjacent drop shaped loop at the contact surface of the adjacent drop shaped loop parallel to the folding longitudinal axis; and
introducing the folded stent along its longitudinal axis into a cylindrical sleeve.

6. The method according to claim 5, wherein the at least three inward pushing portions are spaced at identical angular distances from each other around a circumference of the cylindrical sheet.

* * * * *